United States Patent [19]

Flaugh

[11] Patent Number: 6,022,980

[45] Date of Patent: Feb. 8, 2000

[54] PREPARATION OF 4-HALO AND 6-HALOMELATONINS

[75] Inventor: Michael Edward Flaugh, Indianapolis, Ind.

[73] Assignee: Eli Lilly and Company, Indianapolis, Ind.

[21] Appl. No.: 09/311,404

[22] Filed: May 13, 1999

Related U.S. Application Data

[60] Provisional application No. 60/093,090, Jul. 16, 1998.
[51] Int. Cl.$^7$ ................................................. C07D 209/10
[52] U.S. Cl. .............................................................. 548/402
[58] Field of Search ....................................... 548/402, 406

[56] References Cited

U.S. PATENT DOCUMENTS

| | | | |
|---|---|---|---|
| 4,614,807 | 9/1986 | Flaugh | 548/507 |
| 5,071,875 | 12/1991 | Horn et al. | 514/616 |
| 5,151,446 | 9/1992 | Horn et al. | 514/617 |

*Primary Examiner*—Joseph K. McKane
*Attorney, Agent, or Firm*—Elizabeth A. Dawalt; Robert D. Titus

[57] ABSTRACT

This invention provides an improved process for the preparation and separation of 4-halo and 6-halomelatonins.

17 Claims, No Drawings

PREPARATION OF 4-HALO AND 6-HALOMELATONINS

PRIORITY CLAIM

This application claims the benefit of U.S. Provisional Patent 60/093090, filed Jul. 16, 1998.

BACKGROUND OF THE INVENTION

The characterization of melatonin receptor subtypes [$Mel_{1a}$, $Mel_{1b}$, $Mel_{1c}$] (Dubocovich, M. L., *Trends Pharmacol. Sci.*, 16, pp. 50–56 (1995)) in native tissues has been hampered by the lack of selective ligands that can distinguish between them. The affinity of 2-iodomelatonin for melatonin receptor subtypes stably expressed in CHO cells is considerably higher for the human $Mel_{1a}$ and Xenopus $Mel_{1c}$ subtypes than for the human $Mel_{1b}$ subtype. Radioligands with reduced affinity for the $Mel_{1a}$ and $Mel_{1c}$ receptor subtypes and selectivity for the $Mel_{1b}$ subtype are valuable in the characterization of melatonin receptor subtypes. 4-Iodo- and 6-iodomelatonin have the ability to bind competitively with 2-[$^{125}$I]-iodomelatonin at melatonin receptor subtypes. 4-Iodomelatonin shows a higher affinity for the $Mel_{1b}$ than for the $Mel_{1a}$ or $Mel_{1c}$ melatonin receptor subtypes. On the other hand, 6-iodomelatonin has similar affinities for the $Mel_{1a}$ and $Mel_{1b}$ subtypes but a low affinity for the $Mel_{1c}$ receptor.

Halomelatonins have been prepared by a number of methods well known in the art. The methodology used to synthesize 4- and 6-halomelatonins is unsuitable for the preparation of radioligands because the halogen is introduced at or near the beginning of the synthesis. Furthermore, because of the high susceptibility of the 2-position of the melatonin for electrophilic attack, direct halogenation of melatonin itself results in predominately 2-halomelatonin.

BRIEF SUMMARY OF THE INVENTION

This invention provides an improved process for the preparation and separation of 4-halo and 6-halomelatonins comprising:

a) substituting the 1-position of the melatonin in an appropriate solvent to produce the protected melatonin derivative in which the only indole positions readily available for substitution are the 4- and 6- positions, b) mercurating the protected melatonin derivative in an appropriate solvent with a mercuric salt to produce a mixture of the 4- and 6-organomercury products, c) treating the mixture of 4- and 6-organomercurated products in an appropriate solvent with a halide salt to provide a mixture of the corresponding 4- and 6-halomercury isomers, d) separating in an appropriate solvent the mixture of 4-halomercury and 6-halomercury isomers into the individual 4-halomercury and 6-halomercury isomers, e) treating, in an appropriate solvent, the individual 4-halomercurated and 6-halomercurated isomers with a halogenating agent to produce the corresponding isolated 4- and 6-halogenated derivatives, and f) deprotecting the isolated 4- and 6-halogenated derivatives in an appropriate solvent.

Another embodiment of this invention is the mercury substituted intermediates: the 4- and 6-acetoxymercury products, as represented in FIG. I (where X=acetoxy), the 4- and 6-halomercury isomers, as represented in FIG. I (where X=halogen), and 4- and 6-mercurated melatonin derivatives derivable from the halomercury compounds (FIG. I, where X=trifluoroacetoxy).

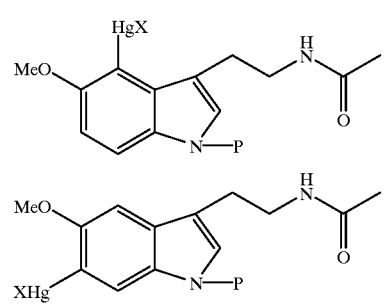

I

DETAILED DESCRIPTION OF THE INVENTION

The invention is useful for the transformation generically represented by the following reaction scheme:

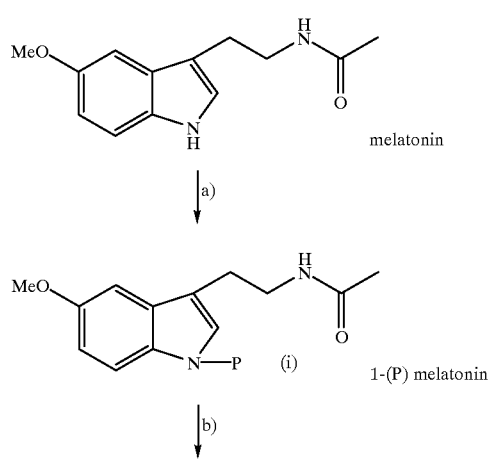

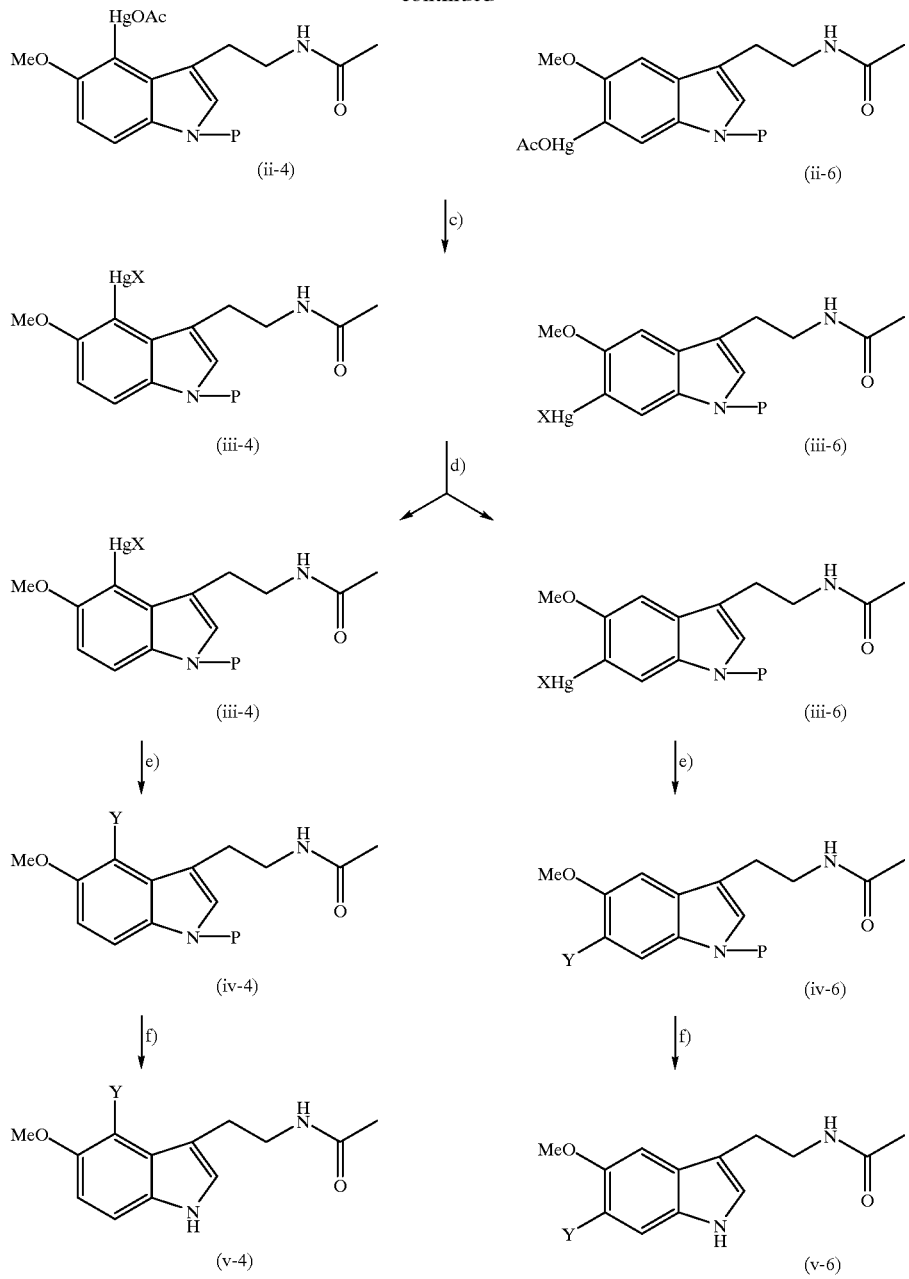

The process of the invention is performed by the following steps:
a) substituting the 1-position of the melatonin in an appropriate solvent to produce the protected melatonin derivative in which the only indole positions readily available for substitution are the 4- and 6- positions,
b) mercurating the protected melatonin derivative in an appropriate solvent with a mercuric salt to produce a mixture of the 4- and 6-organomercury products,
c) treating the mixture of 4- and 6-organomercurated products in an appropriate solvent with a halide salt to provide a mixture of the corresponding 4- and 6-halomercury isomers,
d) separating in an appropriate solvent the mixture of 4-halomercury and 6-halomercury isomers into the individual 4-halomercury and 6-halomercury isomers,
e) treating, in an appropriate solvent, the individual 4-halomercurated and 6-halomercurated isomers with a halogenating agent to produce the corresponding isolated 4- and 6-halogenated derivatives, and
f) deprotecting the isolated 4- and 6-halogenated derivatives in an appropriate solvent.

The process of step a) of the invention is performed by combining melatonin with a strong base and a source useful for applying a protecting group in an appropriate reaction medium. Once the reaction is complete, as measured by consumption of the substrate, the resulting 1-(P)melatonin is isolated by standard extractions and filtrations. If desired, the protected melatonin may be further purified by chromatography or crystallization as appropriate.

As the skilled artisan would appreciate, the melatonin is first treated with the base, then the source of the protecting group. The substrate may first be dissolved in an appropriate reaction medium and treated with base then added to a mixture of the source of the protecting group. Also, a solution of the substrate treated with base in an appropriate reaction medium may be added to a slurry of the source of the protecting group in the same reaction medium. Furthermore, a first slurry containing part of the reactants in an appropriate reaction medium may be added to a second slurry of the remaining reactants in an appropriate reaction medium as is desired or convenient. All of these methods are useful for the process of the present invention.

Reaction media useful for the process of step a) of the invention must be capable of dissolving a sufficient amount of the melatonin and the protecting group for the reaction to proceed. Organic solvents useful as reaction media for the process of this invention include dimethylformamide, diethyl ether, dimethoxyethane, and preferably tetrahydrofuran.

Suitable bases for this transformation are potassium hydride, sodium hydride, n-butyl lithium, t-butyl lithium or phenyl lithium.

The skilled artisan would appreciated that any bulky protecting group, especially large silyl groups such as tri-isopropylsilyl triflate, triisopropylsilyl chloride, t-butyldimethylsilyl chloride or triethylsilyl chloride, are useful compounds as sources for the protecting group for the present invention.

The process of step a) may be carried out over a large range of concentrations, from about 0.001 molar to about 2.0 molar of the protecting group, dependent upon the solubility of the particular protecting group in the chosen reaction medium. The reaction may also be performed on slurries of the protecting group so long as a sufficient amount of the protecting group is soluble in the reaction medium for the reaction to proceed. Preferably the process is performed at a concentration from about 0.01 molar to about 1.0 molar. A concentration of about 0.1 molar to about 0.5 molar is most preferred.

Reactions of step a) may be performed between about −30° and about 60° C., preferably between about 20° C. and about 30° C. The skilled artisan will appreciate that the reaction rates will decrease as temperatures are lowered and increase as temperatures are elevated.

The mercuration process of step b) of the invention is performed by combining the 1-(P)melatonin of step a) with an appropriate mercuric salt in an appropriate reaction medium. Once the reaction has stopped, as measured by TLC, HPLC or NMR, the resulting mixture of ii-4 and ii-6 products is isolated by standard extractions and filtrations. If desired, the mixture of ii-4 and ii-6 products may be further purified by chromatography or crystallization as appropriate.

The order and manner of combining the reactants are not important and may be varied as a matter of convenience. The 1-(P)melatonin and mercuric salt may first be combined and then the reaction medium added. Alternatively, a solution of the substrate in an appropriate reaction medium may be added to a slurry of the mercuric salt in the same reaction medium. Furthermore, a first slurry containing part of one reactant in an appropriate reaction medium may be added to a second slurry of the remaining reactants in an appropriate reaction medium as is desired or convenient. All of these methods are useful for the process of the present invention.

The mercuric salt useful for the present invention include mercuric trifluoroacetate and preferably mercuric acetate.

Reaction media useful for the mercuration process must be capable of dissolving a sufficient amount of the 1-(P) melatonin and mercuric salt for the reaction to proceed. Organic solvents useful as reaction media for the process of this invention include acetic acid, dimethylformamide, and preferably acetonitrile.

Reactions of step b) may be performed between about −30° and about 50° C., preferably between about 20° C. and about 30° C. The skilled artisan will appreciate that the reaction rates will decrease as temperatures are lowered and increase as temperatures are elevated.

The mercuration process of step b) may be carried out over a large range of concentrations, from about 0.001 molar to about 2.0 molar of the mercuric salt. The reaction may also be performed on slurries of the mercuric salt so long as a sufficient amount of the mercuric salt is soluble in the reaction medium for the reaction to proceed. Preferably the process is performed at a concentration from about 0.01 molar to about 1.0 molar. A concentration of about 0.05 molar to about 0.10 molar is most preferred.

The ii-4 and ii-6 products of step b) are difficult to separate. Therefore, the products are converted to iii-4 and iii-6 by the process of step c) and then separated. The process of step c) of the invention is performed by combining the ii-4 and ii-6 products of step b) with an appropriate source of halide ion in an appropriate two-phase reaction medium. Once the reaction is complete, as measured by consumption of the substrate, the resulting mixture of iii-4 and iii-6 products is isolated by standard extractions and filtrations.

The ii-4 and ii-6 products, dissolved in an appropriate medium, may be treated with a source of halide ion. Alternatively, a solution of the substrate in an appropriate reaction medium may be added to a slurry of the source of halide ion in the second medium. All of these methods are useful for the process of the present invention.

Compounds useful for a source of halide ion for the present invention include sodium chloride, potassium chloride, tetrabutylammonium chloride.

Organic solvents useful as reaction media for the process of this invention include methylene chloride, chloroform, and ethyl acetate. The second medium is water.

The process of step c) may be carried out over a large range of concentrations, from about 0.001 molar to about 2.0 molar of the source of halide ion. The skilled artisan would appreciate the desire to use a concentrated source of halide ion. Therefore, concentrations from about 1.0 molar to about 2.0 molar of the source of halide ion are preferred.

A chromatographic method of step d) is used for the separation of isomers by employing florisil or, preferably, silica gel utilizing ethyl acetate or ethyl acetate/hexane.

The process of step e) of the invention is performed by combining the iii-4 or iii-6 product of step d) with an appropriate halogenating agent in an appropriate reaction medium. Once the reaction is complete, as measured by consumption of the substrate, the resulting iv-4 or iv-6 product is isolated by standard extractions and filtrations. If desired, the iv-4 and iv-6 products may be further purified by chromatography or crystallization as appropriate.

The order and manner of combining the reactants may be important depending on the halogenating agent used. The iii-4 and iii-6 products and halogenating agent may first be combined and then the reaction medium added. Alternatively, the substrate may first be dissolved in an appropriate reaction medium and this solution added to a mixture of the halogenating agent. Also, a solution of the substrate in an appropriate reaction medium may be added to a slurry of the halogenating agent in the same reaction medium. But when the halogenating agent is a halide salt in combination with a activating agent, the salt must be added prior to the actvating agent. All of these methods are useful for the process of the present invention.

Halogenating agents useful for the process of step e) are either relatively strong halogenating agents, such as iodine, bromine, fluorine, iodine monochloride, hypohalites, and acylhypohalites, or alkali halides plus oxidants such as chloramine-T or hydrogen peroxide plus a peroxidase enzyme.

Reaction media useful for the process of step e) must be capable of dissolving a sufficient amount of either iii-4 or iii-6 and the halogenating agent for the reaction to proceed. Solvents useful as reaction media for the process of this invention depend upon the choice of halogenating agent and may include alcohols, alcohol/water combinations or chlorocarbons. Depending upon the choice of halogenating agent, reactions of step e) may be performed between about −78° and about 60° C., the preferred temperature depends upon the nature of the halogenating agent. The skilled artisan will appreciate that the reaction rates will decrease as temperatures are lowered and increase as temperatures are elevated.

The process of step e) may be carried out over a large range of concentrations, from about 0.001 molar to about 2.0 molar of the halogenating agent, dependent upon the solubility of the particular halogenating agent in the chosen reaction medium. Preferably the process is performed at a concentration from about 0.01 molar to about 1.0 molar. A concentration of about 0.30 molar to about 0.50 molar is most preferred.

The deprotection process of step f) of the invention is performed by combining the iv-4 or iv-6 product of step e) with an appropriate deprotecting compound in an appropriate reaction medium. Once the reaction is complete, as measured by consumption of the substrate, the resulting v-4 or v-6 product is isolated by standard extractions and filtrations. If desired, the v-4 and v-6 products may be further purified by chromatography or crystallization as appropriate.

The order and manner of combining the reactants are not important and may be varied as a matter of convenience. The iv-4 and iv-6 products and deprotecting compound may first be combined and then the reaction medium added. Alternatively, the substrate may first be dissolved in an appropriate reaction medium and this solution added to a mixture of the deprotecting compound. Also, a solution of the substrate in an appropriate reaction medium may be added to a slurry of the deprotecting compound in the same reaction medium. Furthermore, a first slurry containing part of the reactants in an appropriate reaction medium may be added to a second slurry of the remaining reactants in an appropriate reaction medium as is desired or convenient. All of these methods are useful for the process of the present invention.

Compounds useful as deprotecting compounds, those compounds which cleave the protecting group from the melatonin derivative, depends on the protecting group used, as the skilled artisan would appreciate. For example, trifluoroacetic acid, cesium fluoride, pyridine hydrofluoride, or tetrabutylammonium fluoride will remove a silyl protecting group. However, tetrabutylammonium fluoride is preferred.

Reaction media useful for the process of step f) must be capable of dissolving a sufficient amount of the iv-4 or iv-6 products for the reaction to proceed. Organic solvents useful as reaction media for the process of this invention depend upon the choice of deprotecting agent and may include tetrahydrofuran, acetonitrile or chlorocarbons.

Depending upon the choice of deprotecting agent, reactions of step f) may be performed between about −30° and about 60° C. The skilled artisan will appreciate that the reaction rates will decrease as temperatures are lowered and increase as temperatures are elevated.

The process of step f) may be carried out over a large range of concentrations, from about 0.001 molar to about 2.0 molar of the iv-4 or iv-5 products, dependent upon the solubility of the particular product in the chosen reaction medium. Preferably the process is performed at a concentration from about 0.01 molar to about 1.0 molar. A concentration of about 0.20 molar to about 0.50 molar is most preferred.

The advantage of the process of the invention is achieved by the addition of a protecting group that prevents mercuration of the 1-, 2- and 7-positions of the melatonin intermediate, allowing for the ultimate addition of the halogen only to the 4- and 6-positions. Another advantage of the process of the invention is achieved by the addition of the halogen at or near the end of the reaction scheme, after isolation of the 4- and 6-organomercuric melatonin derivatives. These advantages are best demonstrated by comparing the reaction schemes with and without the addition of a protecting group and addition of the halogen at or near the beginning of the reaction scheme. Without the protecting group, the skilled artisan would appreciate the high susceptibility of the 2-position of melatonin for electrophilic attack. Therefore, without the protecting group, treatment of melatonin with an organomercuric reagent would yield mercuration predominately at the 2-position. Treatment of the protected melatonin derivative with a mercurating reagent produced the 4- and 6-organomercurated products in a ratio of about 2.5 to 1.

The following examples are illustrative only, and are not intended to limit the scope of the invention in any way.

EXAMPLE 1

Synthesis of 1-Triisopropylsilylmelatonin

A portionwise addition of 2.00 g (17.5 mmol) of a 35 wt. % dispersion of KH in mineral oil was made to a solution of 2.00 g (8.62 mmol) of melatonin in 30 mL of tetrahydrofuran. The mixture was stirred until there was no further evidence of reaction. The resulting slurry was treated with 2.70 ml (5.30 g, 17.2 mmol)of triisopropylsilyl triflate. The reaction was stirred overnight.

The reaction was worked up by adding it to dilute aqueous $Na_2CO_3$ and extracting the product into $CH_2Cl_2$. The extract was washed with NaCl solution, then dried over $Na_2SO_4$. The $CH_2Cl_2$ was evaporated leaving a viscous oil. The oil was chromatographed over 400 g of silica gel using ethyl acetate. The purified product from the column weighed 3.02 g (90% yield). It was followed by 0.058 g of starting material. Upon standing, the product crystallized.

m.p.: 127–128.5° C.; MS (esi+), m/e=389.4 (M+1); Analysis for $C_{22}H_{36}N_2O_2Si$: Calculated: C, 67.99; H, 9.34; N, 7.21; Found: C, 68.76; H, 9.66; N, 7.50.

EXAMPLE 2

Synthesis of 4-Chloromercury-1-triisopropylsilylmelatonin and 6-Chloromercury-1-triisopropylsilylmelatonin A mixture of 2.80 g (7.22 mmol) of 1-triisopropylsilylmelatonin and 50 ml of acetonitrile was treated with 2.80 g (8.78 mmol)of Hg(OAc)2. After stirring for 48 h, the mixture was filtered, and the solid was washed with $CH_2Cl_2$. The filtrate and washings were diluted with water and extracted thoroughly with $CH_2Cl_2$, filtering to remove precipitated solid as necessary. The extracts were dried over $Na_2SO_4$. Evaporation of the extracts gave 4.5 g of viscous oil consisting of starting material, the desired 4-acetoxymercury and 6-acetoxymercury derivatives and some 4,6-bis-acetoxymercury compound. [In a separate experiment, the starting material and the bis-mercurated material were separated from this mixture of mono-acetoxymercury derivatives by chromatographing over florisil using ethyl acetate, then mixtures of methanol and ethyl acetate containing progressively higher concentrations of methanol, then 100% methanol, and finally 5% HOAc in methanol- The mixture of mono-acetoxymercury derivatives were recovered in 50% yield from the HOAc/methanol solutions.] The 4.5 g of crude mercurated products were applied to a column of 400 g of silica gel with $CHCl_3$. Eluting the column with 2% methanol in $CHCl_3$ afforded 0.61 g of starting material. A solution of 8.0 g of triethylbenzylammonium chloride in 20 mL of $CHCl_3$ was then applied to the column, and the column was eluted with 4% methanol in $CHCl_3$, which quickly produced fractions containing pure 6-chloromercury-1-triisopropylsilylmelatonin, followed by mixtures of 6-chloro- and 4-chloromercury-1-triisopropylsilylmelatonin, followed by pure 4-chloromercury-1-triisopropylsilylmelatonin. The fractions containing both products were rechromatographed over silica gel using ethyl acetate to complete the separation. The 4-chloromercury-1-triisopropylsilylmelatonin was recrystallized from hexane/toluene affording 2.01 g (55% yield, correcting for recovered starting material) of crystalline product. The 6-chloromercury-1-triisopropylsilylmelatonin was recrystallized from toluene giving 0.72 g (20% yield, correcting for recovered starting material) of crystalline product.

4-Chloromercury-1-triisopropylsilylmelatonin:

m.p.: 164–165° C.; MS (fd+), m/e=626.01 (47%), 624.00 (100, M+), 623.03 (34), 623.00 (32), 621.99 (66), 620.97 (36); Analysis for $C_{22}H_{35}ClHgN_2O_2Si$: Calculated: C, 2.37; H, 5.66; N, 4.49; Found: C, 42.20; H, 5.68; N, 4.38.

6-Chloromercury-1-triisopropylsilylmelatonin:

m.p.: 207–208° C.; MS (fd+), m/e=626.14 (44%), 625.13 (33), 624.14 (100, M+), 623.97 (81), 623.10 (67), 62.11 (70), 621.96 (61); Analysis for $C_{22}H_{35}ClHgN_2O_2Si$: Calculated: C, 42.37; H, 5.66; N, 4.49; Found: C, 42.34; H, 5.69; N, 4.27.

EXAMPLE 3

Synthesis of 4-Iodo-1-triisopropylsilylmelatonin

A) A solution of 0.200 g (0.32 mmol) of the 4-chloromercury derivative from Example 2 in 5.0 mL of ethanol was stirred at 0° C. as a solution of 0.082 g (0.33 mmol) of iodine in 2.0 mL of ethanol was added dropwise. The faintly yellow solution was diluted with cold water, and the product was extracted into $CH_2Cl_2$. The extract was washed with water and dried over $Na_2SO_4$. Evaporation of the $CH_2Cl_2$ afforded the product as a colorless oil, however there were small yellow crystals present in the product. These crystals were removed by dissolving the product in toluene/hexane and decanting. The product was further purified by chromatographing over silica gel using 1:1 hexane/ethyl acetate. The purified 4-iodo-1-triisopropylsilylmelatonin was a viscous oil weighing 0.146 g (89% yield).

MS (esi+), m/e=515.3 (76%, M+1), 388.35 (100, loss of I); Analysis for $C_{22}H_{35}IN_2O_2Si$: Calculated: C, 51.36; H, 6.86; N, 5.44; I, 24.66; Found: C, 51.11; H, 6.71; N, 5.38; I, 24.60.

B) A mixture of 0.200 g (0.32 mmol) of the 4-chloromercury derivative from Example 2 and 0.55 g (0.37 mmol) of NaI in 10.0 mL of ethanol was stirred at 0° C. as a solution of 0.099 g (0.35 mmol) of chloramine-T trihydrate in 0.5 mL of water was added dropwise. The solution was stirred at 0° C. for an hour. It was then poured into dilute aqueous NaCl solution, and the product was extracted into $CH_2Cl_2$. The cloudy extract was filtered through Celite, then evaporated to a viscous residue. Chromatography as in procedure A gave 0.92 g (56% yield) of 4-iodo-1-triisopropylsilylmelatonin as a colorless oil. The material from this procedure was contaminated with a minor amount of starting material but was suitable for conversion to 4-iodomelatonin.

EXAMPLE 4

Synthesis of 6-Iodo-triisopropylsilylmelatonin

A) A suspension of 0.200 g (0.32 mmol) of the 6-chloromercury derivative from Example 2 in 5 ml of ethanol was stirred at 0° C. as a solution of 0.082 g (0.33 mmol) of iodine in 2 ml of ethanol was added dropwise. The 6-chloromercury derivative gradually dissolved leaving a clear, colorless solution as the end of the addition was reached. The solution was diluted with cold water, and the product was extracted into $CH_2Cl_2$. The extract was washed with water and dried over $Na_2SO_4$. Evaporation of the $CH_2Cl_2$ afforded the product as a colorless solid. The product was further purified by chromatographing over silica gel using ethyl acetate. The purified 4-iodo-1-triisopropylsilylmelatonin was a colorless, crystalline solid weighing 0.172 g (quantitative yield).

m.p.: 136–138.5° C.; MS (esi+), m/e=515.4 (100%, M+1) Analysis for $C_{22}H_{35}IN_2O_2Si$: Calculated: C, 51–36; H, 6.86; N, 5.44; I, 24.66; Found: C, 51.27; H, 6.76; N, 5.44; I, 24.59.

B) Treating 0.200 g (0.32 mmol)of the 6-chloromercury derivative according to procedure B in Example 3 afforded, after silica gel chromatography using and recrystallization from toluene/hexane, 0.110 mg (67% yield) of 6-iodo-1-triisopropylsilylmelatonin. The material from this procedure was contaminated with a minor amount of starting material but was suitable for conversion to 6-iodomelatonin.

EXAMPLE 5

Synthesis of 4-Iodomelatonin

A solution of 0.133 g (0.26 mmol) of the 4-iodo-1-triisopropylsilylmelatonin in 7 mL of tetrahydrofuran was treated with 0.50 mL of 1M tetrabutylammonium fluoride in tetrahydrofuran at 0° C. After an hour, the solution was diluted with water, and the product was extracted into $CH_2Cl_2$. The extract was washed with water, dried over $Na_2SO_4$, and then evaporated to a clear oil. The product was purified by chromatographing over silica gel using ethyl acetate. It was then recrystallized from ethyl acetate. The recrystallized 4-iodomelatonin weighed 0.83 g (89% yield).

m.p.: 144–145° C. MS (esi+), m/e=359.13 (34%, M+1), 232.15 (100, loss of I); Analysis for $C_{13}H_{15}IN_2O_2$: Calculated: C, 43.59; H, 4.22; N, 7.82; I, 35.43; Found: C, 43.84; H, 4.23; N, 7.71; I, 35.59.

EXAMPLE 6

Synthesis of 6-Iodomelatonin

A solution of 0.150 g (0.29 mmol) of the 6-iodo-1-triisopropylsilylmelatonin, in 7 mL of tetrahydrofuran was treated at 0° with 0.50 mL of 1M tetrabutylammonium fluoride in tetrahydrofuran. After an hour, the solution was diluted with water, and the product was extracted into chloroform. The extract was washed with water, dried over Na₂SO₄, and then evaporated to a clear oil. The product was purified by chromatographing over silica gel using ethyl acetate. The product from the chromatography was a colorless oil that crystallized slowly upon standing. The product was recrystallized by dissolving in CHCl₃, evaporating to an oily residue, and then triturating with toluene. The recrystallized 4-iodomelatonin weighed 0.90 g (87% yield).

m.p.: 131–132° C. MS (fd+), m/e=357.98 (100%, M+); Analysis for $C_{13}H_{15}IN_2O_2$: Calculated: C, 43.59; H, 4.22; N, 7.82; I, 35.43; Found: C, 43.74; H, 4.22; N, 7.70; I, 35.15.

EXAMPLE 7

Synthesis of 4-Acetoxymercury-1-triisopropylsilylmelatonin

A solution of 0.100 g (0.16 mmol) of the 4-chloro-1-triisopropylsilylmercury in 10 mL of $CH_2Cl_2$ was washed nine times with 10 mL portions of 2M sodium acetate solution, counterextracting each wash with fresh $CH_2Cl_2$. The organic solution was dried over Na₂SO₄, then evaporated leaving a quantitative yield of 4-acetoxymercury-1-triisopropylsilylmelatonin as a colorless foam.

IR (CHCl₃), ν=1659 cm⁻¹, 1631, 1575, 1413; MS (fd+), m/e=1175.06 (79%, dimer—2 OAc), 975.67 (100, dimer—Hg & 2OAc), 589.85 (5.5), 588.65 (5.4), 587.90 (18.0, loss of OAc), 587.16 (13.8), 585.74 (3.4), 585.21 (7.2), 388.41 37, loss of HgOAc); Analysis for $C_{24}H_{38}HgN_2O_4Si$: Calculated: C, 44.54; H, 5.92; N, 4.33; Found: C, 44.67; H, 5.78; N, 4.40.

EXAMPLE 8

Synthesis of 6-Acetoxymercury-1-triisopropylsilylmelatonin

Treating 0.100 g (0.16 mmol) of the 6-chloro-1-triisopropylsiylmercury according to the procedure in Example 7 afforded a quantitative yield of 6-acetoxymercury-1-triisopropylsilylmelatonin, also isolated as a colorless foam.

IR (CHCl₃), ν=1666 cm⁻¹, 1575, 1421; MS (fd+), m/e= 1175.13 (40%, dimer—2 OAc), 973.62 (100, dimer—Hg & 2OAc), 589.61 (2.4), 588.81 (5.9), 588.09 (14.3, loss of OAc), 587.26 (2.6), 586.70 (4.4), 586.29 (6.7), 388.41 (23, loss of HgOAc); Analysis for $C_{24}H_{38}HgN_2O_4Si$: Calculated: C, 44.54; H, 5.92; N, 4.33; Found: C, 45.54; H, 6.03; N. 4.48.

EXAMPLE 9

Synthesis of 4-Trifluoroacetoxymercury-1-triisopropylsilylmelatonin

A solution of 0.100 g (0.16 mmol) of the 4-chloro-1-triisopropylsilylmercury in 3.0 mL of methanol was treated with a solution of 0.0355 g (0.16 mmol) of freshly dried silver trifluoroacetate in 2.0 mL of methanol. After allowing to stand for 15 min., the mixture was filtered through Celite. The filtrate was evaporated to a viscous oil. This oil was taken up in 5 mL of $CH_2Cl_2$ and refiltered. Evaporation of the $CH_2Cl_2$ gave 0.109 g (97% yield) of 4-trifluoroacetoxymercury-1-triisopropylsilylmelatonin as a colorless foam.

IR (CHCl₃), ν=1692 cm⁻¹, 1667, 1525, 1413; Analysis for $C_{22}H_{35}F_3HgN_2O_4Si$: Calculated: C, 41.11; H, 5.03; N, 3.99; Found: C, 41.23; H, 5.26; N, 4.21.

I claim:

1. A process for the synthesis of substituted 4- and 6-position melatonin compounds, comprising:

a) substituting the 1-position of the melatonin in an appropriate solvent to produce the protected melatonin compound in which the only indole positions readily available for substitution are the 4- and 6- positions, b) mercurating the protected melatonin compound in an appropriate solvent with a mercuric salt to produce a mixture of the 4- and 6-organomercury products, c) treating the mixture of 4- and 6-organomercurated products in an appropriate solvent with a halide salt to provide a mixture of the corresponding 4- and 6-halomercury isomers, d) separating in an appropriate solvent the mixture of 4-halomercury and 6-halomercury isomers into the individual 4-halomercury and 6-halomercury isomers, e) treating, in an appropriate solvent, the individual 4-halomercurated and 6-halomercurated isomers with a halogenating agent to produce the corresponding isolated 4- and 6-halogenated compounds, and f) deprotecting the isolated 4- and 6-halogenated compounds in an appropriate solvent.

2. The process of claim 1 wherein the protected melatonin compound is selected from the group consisting of 1-(t-butyldimethylsilyl) melatonin, 1-triisopropylsilyl melatonin, and 1-triethylsilyl melatonin.

3. The process of claim 1 wherein the mercuric salt of step b) is selected from the group consisting of mercuric acetate and mercuric trifluoroacetate.

4. The process of claim 3 wherein the mercuric salt of step b) is mercuric acetate.

5. The process of claim 1 wherein the solvent of step b) is selected from the group consisting of acetic acid, dimethylformamide, and acetonitrile.

6. The process of claim 5 wherein the solvent is acetonitrile.

7. The process of claim 1 wherein the halide salt of step c) is selected from the group consisting of sodium chloride, potassium chloride, triethylbenzylammonium chloride, and tetrabutylammonium chloride.

8. The process of claim 7 wherein the halide salt of step c) is triethylbenzylammonium chloride.

9. The process of claim 1 wherein the halogenating agent of step e) is selected from the group consisting of iodine, bromine, fluorine, iodine monochloride, hypohalites, acylhypohalites, and alkali halides plus oxidants.

10. The process of claim 9 wherein the oxidants are selected from the group consisting of chloramine-T and hydrogen peroxide plus a peroxidase enzyme.

11. The process of claim 9 wherein the alkali halide plus oxidant of step e) is sodium iodide plus chloramine-T.

12. The process of claim 1 wherein the solvent of step e) is selected from the group consisting of alcohol, alcohol/water combinations, and chlorocarbons.

13. The process of claim 12 wherein the solvent is ethanol.

14. A compound of the formula:

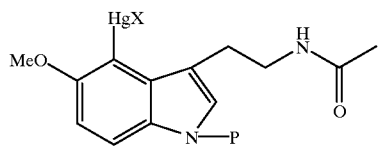

wherein P is selected from the group consisting of triisopropylsilyl, t-butyldimethylsilyl and triethylsilyl, and X is selected from the group consisting of chloro, acetoxy and trifluoroacetoxy.

15. The compound of claim 14 wherein P is triisopropylsilyl and X is chloro.

16. A compound of the formula:

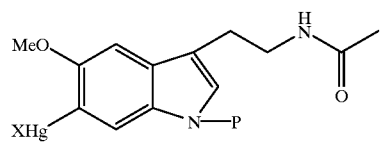

wherein P is selected from the group consisting of triisopropylsilyl, t-butyldimethylsilyl and triethylsilyl, and X is selected from the group consisting of acetoxy and trifluoroacetoxy.

17. The compound of claim 16 wherein P is triisopropylsilyl and X is chloro.

* * * * *

UNITED STATES PATENT AND TRADEMARK OFFICE
CERTIFICATE OF CORRECTION

PATENT NO.   : 6,022,980
DATED        : February 8, 2000
INVENTOR(S)  : Michael Edward Flaugh It is certified that error appears in the above-indentified patent and that said Letters Patent is hereby corrected as shown below:

In column 13, line 5, please delete "MeO" from the structure and insert therefor -- OMe --.

In column 14, line 5, please delete "MeO" from the structure and insert therefor -- OMe --.

Signed and Sealed this

Third Day of April, 2001

Attest:

NICHOLAS P. GODICI

Attesting Officer

Acting Director of the United States Patent and Trademark Office